(12) United States Patent
Tanaka

(10) Patent No.: US 9,668,838 B2
(45) Date of Patent: Jun. 6, 2017

(54) DENTAL BLOCK

(71) Applicant: Tanaka Dental Products, Skokie, IL (US)

(72) Inventor: Asami Tanaka, Skokie, IL (US)

(73) Assignee: Asami Tanaka Dental, Skokie, IL (US)

( * ) Notice: Subject to any disclaimer, the term of this patent is extended or adjusted under 35 U.S.C. 154(b) by 124 days.

(21) Appl. No.: 14/251,621

(22) Filed: Apr. 13, 2014

(65) Prior Publication Data

US 2014/0300014 A1 Oct. 9, 2014

Related U.S. Application Data

(63) Continuation of application No. 12/950,997, filed on Nov. 19, 2010, now Pat. No. 8,696,954, and a continuation of application No. PCT/US2012/069960, filed on Dec. 15, 2012.

(60) Provisional application No. 61/353,035, filed on Jun. 9, 2010, provisional application No. 61/570,825, filed on Dec. 15, 2011.

(51) Int. Cl.
*A61C 13/08* (2006.01)
*A61C 13/083* (2006.01)
*A61K 6/00* (2006.01)
*A61K 6/02* (2006.01)
*A61K 6/027* (2006.01)
*C04B 41/85* (2006.01)
*C04B 41/00* (2006.01)
*C04B 41/45* (2006.01)
*A61C 19/10* (2006.01)
*C04B 111/00* (2006.01)
*C04B 111/82* (2006.01)

(52) U.S. Cl.
CPC .......... *A61C 13/081* (2013.01); *A61C 13/082* (2013.01); *A61C 13/083* (2013.01); *A61K 6/0017* (2013.01); *A61K 6/0094* (2013.01); *A61K 6/023* (2013.01); *A61K 6/0225* (2013.01); *A61K 6/0255* (2013.01); *A61K 6/0273* (2013.01); *C04B 41/009* (2013.01); *C04B 41/4535* (2013.01); *C04B 41/85* (2013.01); *A61C 13/08* (2013.01); *A61C 19/10* (2013.01); *C04B 2111/00836* (2013.01); *C04B 2111/82* (2013.01)

(58) Field of Classification Search
CPC ..... A61C 13/081; A61C 13/083; A61C 13/08; A61C 19/10; A61K 6/0255; A61K 6/023; A61K 6/0225; A61K 6/0094; A61K 6/0017; A61K 6/0273; A71C 13/082
USPC ...................................................... 264/16, 20
See application file for complete search history.

(56) References Cited

U.S. PATENT DOCUMENTS

| | | | | |
|---|---|---|---|---|
| 2,682,480 A | * | 6/1954 | Andrews | C03C 8/16 106/219 |
| 8,178,012 B1 | * | 5/2012 | Khan | A61C 13/082 264/16 |
| 2002/0110787 A1 | * | 8/2002 | Abiru | A61K 6/0032 433/224 |
| 2003/0215770 A1 | * | 11/2003 | Sekino | A61C 5/10 433/218 |

(Continued)

*Primary Examiner* — Nahida Sultana

(57) ABSTRACT

A system, method and composition for making a dental ceramics block. The system, method, and composition resulting in natural color matching without drying time between color layers. The system, method and composition also resulting in good color preparation on restorations of about 0.001 mm-1.000 mm thickness.

12 Claims, 5 Drawing Sheets

(56) References Cited

U.S. PATENT DOCUMENTS

| | | | |
|---|---|---|---|
| 2006/0058417 A1* | 3/2006 | Brandenburg | A61K 6/0017 523/116 |
| 2006/0083694 A1* | 4/2006 | Kodas | B01J 13/0043 424/46 |
| 2010/0068674 A1* | 3/2010 | Zucker | A61C 8/005 433/173 |
| 2013/0225699 A1* | 8/2013 | Bublewitz | A61K 6/0017 514/772.4 |

* cited by examiner

DENTAL BLOCK

RELATED APPLICATIONS

The present patent document is a continuation of PCT Application Serial No. PCT/US12/69960, filed Dec. 15, 2012, designating the United States and published in English, which is hereby incorporated by reference. PCT Application Serial No. PCT/US12/69960, filed Dec. 15, 2012 claims the benefit of the filing date of Provisional U.S. Patent Application Ser. No. 61/570,825 filed Dec. 15, 2011.

The present patent document is a continuation of application Ser. No. 12/950,997, filed Nov. 19, 2010, which claims the benefit of the filing date under 35 U.S.C. §119(e) of Provisional U.S. Patent Application Ser. No. 61/353,035, filed Jun. 9, 2010. All of the foregoing applications are hereby incorporated by reference in their entirety.

BACKGROUND

Often during sporting, automobile accidents, or due to illness or disease, individuals may lose one or more teeth. The loss of teeth may result in loss of integrity of the bite. Also, many individuals are uncomfortable with the appearance of missing teeth. The dental arts have established technology to create artificial teeth that mimic an individual's original teeth. For example, the dental arts, using ceramics, can mold teeth that look mimic natural teeth.

Among others, zirconia is a popular material from which dental replacements are made. However, zirconia creates a very hard surface, which is not easily colored. Zirconia also requires firing at temperatures over 900° C. At that temperature, the pigments traditionally used to color dental ceramics disappear and lose color. Presently it is the knowledge of that art that no stains or other colorants will adhere or bond to Zirconia ceramics.

Zirconia is a very strong material and the dental sciences are quickly adopting zirconia ceramics for use in dental restorations. However, a drawback to the use of zirconia is the stark white color of the material. Most individuals prefer dental restorations which have the appearance and color of a natural tooth. Specifically, individuals wish to have dental restorations that blend in naturally with the remaining teeth.

BRIEF SUMMARY

A system, method and composition for coloring dental ceramics. The system, method, and composition resulting in natural color matching without drying time between color layers. The system, method and composition also resulting in good color preparation on restorations of about 0.001 mm-1.000 mm thickness.

DETAILED DESCRIPTION

Figure 1:
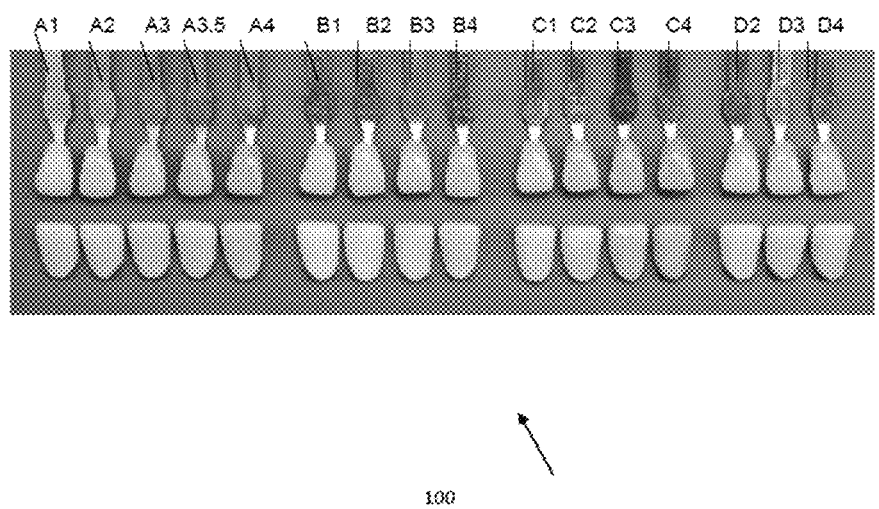
FIG. 1 illustrates the range of natural colors achieved with the disclosed system, method, and composition.

Dental restoration after tooth loss is quite popular to improve the visible appearance of the face and also to restore the integrity of the bite. Individuals who have suffered tooth loss may want their restorations to have a natural appearance and match in size, shape, and color, their natural teeth. Aesthetically pleasing replacements are increasingly sought after.

Technologies, such as CAD/CAM technology may be used in dentistry to help dentists and dental technicians fabricate precise shapes and sizes for dental restorations, including, for example, inlays, onlays, crowns, and bridges. Dentists may use CAD/CAM and other related technologies to provide their patients with durable, well-fitted single and multiple tooth restorations.

Dentists and dental technicians may use CAD/CAM and other technologies to design the anatomical features, size, and shape of a tooth restoration, for example but not limited to, on a computer. For example, with CAD/CAM, the machine fabricates the restoration through a milling chamber that crafts the tooth-like ceramic material into a precise replica of the drawing.

There are many different materials used for making dental restorations. Among them, ceramic may be used for in-lays, on-lays, crowns, veneers, as well as full restorations, among others. For example, full ceramic restorations are particularly desirable because their color and translucency mimic natural tooth enamel.

Computerized dentistry, such as by the use of CAD/Cam technology, has enabled the application of zirconia-oxid ($ZrO_2$). The introduction of this zirconia in restorative and prosthetic dentistry may have encouraged the use of full ceramics without limitation. With the exception of zirconia-oxide, existing ceramics systems may lack reliable potential for the various indications for bridges without size limitations. Zirconia-oxide with its high strength and comparatively higher fracture toughness may be more reliable than existing ceramic systems. With a three-point bending strength exceeding 900 megapascals, zirconia-oxide may be used in virtually every full ceramic prosthetic solution, including bridges, implant supra structures and root dowel pins.

As technology improves, more stringent requirements are being placed on the aesthetics of teeth. Metals and porcelain may currently be the materials of choice for crowns and bridges. The demand for full ceramic solutions, however, continues to grow. Consequently, industry and science are increasingly compelled to develop full ceramic systems. In introducing full ceramic restorations, such as base structures made of sintered ceramics, more attention must be focused on developing a coloring system that improves the natural appearance of the ceramics.

The super hard surface that makes zirconia appealing for ceramic restorations, does not lend itself to easy coloration. Disclosed herein is a method, system, and composition that may be used to impart a natural color to dental restorations. The method, system, and device may eliminate the need to use mask layers of opaque and body porcelains. The method, system, and solution may be capable of preparation on the edge of a knife and may eliminate the need to shoulder prep for color.

A natural tooth, when being prepared for restoration, is reduced in size so it can accept a crown.

Additionally, the method, system, and composition may require short or no drying time and multiple applications of different shades may be possible. Application of the method, system, and composition may result in a three dimensional appearance of the dental restoration that more closely resembles an individuals natural teeth than the currently available coloring systems. Traditionally, this crown comprised layers: a metal cap or understructure for strength and support; a dentin-colored opaque layer to mask the metal; a body porcelain layer; an enamel porcelain layer; and a glaze finish.

With the advent of zirconia as a viable (strong, biocompatible) replacement material for the increasingly expensive metal component, Porcelain-Fused-to-Zirconia restorations have become alternatives to porcelain-fused-to-metal dental prostheses. Without dark metal copings, there is lesser need to use multiple layers of glass ceramic for masking and imparting visual depth. Demand has grown for techniques and materials to transform the white, opaquish material into a more natural looking tooth replacement. Dentin-shaded zirconia colorants and blanks have entered the market to help address this need.

One of the goals of esthetic dentistry is to produce life-like restorations. This necessitates fabricating crowns which seem natural in texture and color. But these are not the only appearance factors which must be duplicated. Translucency as a visual component is of critical importance but is a difficult effect to achieve.

As a general rule, a natural tooth is darker and more opaque in its gingival region; lighter and more translucent at its incisal edge. The process of dental restoration utilizes both internal and external coloring techniques. And, as pre-sintered zirconia is porous and can absorb colorant as a function of time and intensity, shading can be achieved both internally and at the surface.

Today's dental zirconia blanks are available in white and dentin shades. However, as discussed above, these herein, these blanks do not provide optimum restoration and require expensive and time consuming after-processing. While either type can be utilized in the construction of Porcelain-Fused-to-Zirconia crowns, they require a sufficient number of overlying layers of glass ceramic to conceal, mask or adjust the color of the understructures. Dentin-colored blanks are therefore not suitable for the fabrication of Full Contour Crowns, as there is insufficient thickness and a lack of porcelain layering to modify the relatively dark orange shade of the dentin-colored zirconia material. The use of plain white zirconia blanks for these restorations, as well as for Porcelain-Fused-to-Zirconia Crowns, requires much time, effort, material and skill to obtain a convincing result. With the increasing popularity of zirconia restorations, especially of Full Contour Crowns, the need for a novel, more easily workable zirconia blank arises.

We disclose an enamel-colored zirconia blank, the means of producing which can include a doping method that uniformly imparts color to pre-pressed zirconia powder. It is unique in that it moves away from the dark or opaquish appearance of currently available blanks to the color of dental enamel, which is the most difficult to achieve aspect of tooth color reproduction. Theoretically and practically, one can more easily opacify than clarify zirconia with the addition of color; and it is easier to darken than to lighten zirconia by the application of pigment. Producing the enamel coloration of a crown's ⅓ incisal portion is much more technique-sensitive and critical than achieving the orangish ivory of the gingival portion. By starting with an enamel colored blank, the hardest part of the crown coloring process is eliminated, and a more consistent, predictable result can be achieved.

A finished crown must contain both the light blue grey coloring of the ⅓ incisal portion as well as the darker orangish ivory of the gingival portion. Results are more natural and achievable when orange colorant is applied to an enamel colored blank than when an attempt is made to cover an orange substrate with translucent incisal colorant. Orange can always be added, but it can seldom be subtracted, attempting to cover it usually results in an even darker shade of lower value. And an incisal translucent effect is more realistic when it appears to come from within rather than having been applied to the surface.

The strength of zirconia, coupled with the need for fewer layers, has also made it possible to have thinner crowns. This in turn allows more conservative, less invasive preparation of the natural dentition to be restored. The development of Full Contour Crowns—tooth-shaped zirconia with no porcelain overlay—provides a second option for zirconia restoration.

The systems disclosed herein may provide a system of coloring ceramics without the use of harmful acids that are present in currently known systems. The advantage of this is the reduction of acid also reduces damages to equipment and tools used in ceramic arts.

Variations of the system is disclosed. A first system relates to pre-sintering coloring of dental ceramics. A second system relates to post-sintering coloring of dental ceramics. Also disclosed is a method of minimally invasive dental restoration. A third system relates to imparting a fluorescent finish to ceramics, for example but not limited to, zirconia and porcelain ceramics.

Pre-Sintering Coloring of Dental Ceramics

Dental restorations are commonly prepared with a substructure of a metal or ceramic material upon which substructure layers of porcelain are applied. For example, ceramic or metal alloy substructures may be first covered by an opaque layer, followed by an opacious dentin layer, a dentin layer and finally an incisal porcelain layer.

Aesthetics of the dental restoration is of great importance. Patients desire a natural appearance of the prosthesis. In order to achieve a natural appearance of the prosthesis, the dental technician must carefully match and color the framework or facing ceramics. A natural appearance relies not only on color, but on translucence. Currently, most coloring systems require several procedures and layers, which are finally fired (sintered) in an oven. The current coloring systems are therefore time consuming and expensive. Additionally, the current coloring systems may not provide a satisfactory level of natural appearance. For example, dental implants created under current coloring systems often have a shadow from the cast metal. Increased numbers of ceramic layers may be used to mask the shadow from the cast metal, however, to accommodate the increased number of layers, the dental professional must remove an equivalent amount of tooth material. The removal of tooth material, for example, removal of enamel that compromises the integrity of the dentine layer, has lead to the observation that over 22% of restored teeth decay after 5 years.

We disclose herein a dental restoration color system that allows for a natural tooth color result with less preparation time, increased color stability upon firing, and requiring less material therefore less invasive tooth preparation.

The disclosed system is particularly applicable to zirconia restorations, due to the coloring difficulties inherent to zirconia—however, the disclosed system may be used with porcelain or other traditional ceramics with similar results. While we primarily focus our disclosure on use with zirconia, we do not limit the scope of our claims to the use of our disclosed systems and methods to only zirconia ceramics. Zirconia restorations provide increased strength and better fit while also having excellent biological compatibility, which may prevent or reduce gum erosion.

A coloring system for dental ceramics may include may include, among other items, a series of color liquids. The color liquids may be formulated in a wide range of incisal and gingival shades for color matching natural dentition, see FIG. 1, 100 for a visual example of one variation of color shades disclosed herein. The series of color liquids may be given reference numerals for identification of the color of the natural dentition. An example of a series of reference numerals may be: A1, A2, A3, A3.5, A4, B1, B2, B3, B4, C1, C2, C3, C4, D2, D3, D4, Incisal Light, Incisal Dark, Occlusal, and Pink. See FIG. 1.

The liquid compositions of the system may be formulated to dry quickly and may not require preheating prior to sintering. The removal of the preheating requirement may sharply decrease the time required for preparation of restorations. Quick drying may also sharply decrease the time and increase the efficiency of the restoration color matching process. The liquid compositions of the system may be applied by dipping or may be applied by brushing, spraying, or any other way. Application of the liquid composition by brushing may allow for the application of different shades both inside and outside of the restoration.

Dental restoration materials may be provided in blocks of material, for example, dental zirconia ceramic blocks. Dental equipment, such as the CAD/CAM technology, may be used to mill the solid blocks of the restoration material, for example but not limited to zirconia ceramic, into a dental restoration such as but not limited to a bridge, tooth, cap, or other structure.

In one example of preparation of dental restorations, a block of material, for example, a dental zirconia ceramic block or disk, may be prepared by, for example, cold isostatic pressing of zirconia powders. Other pressing methods may also be employed. Cold isostatic pressing, a method by which the blocks are formed under pressure from all sides in a semi-rigid mold, may result in blocks with improved and uniform density as compared to pressing methods that do not apply pressure from all sides.

CAD/CAM restorations may be milled from solid blocks of white composite resin or may be made from porcelain matching the shade of the restored tooth using the process of creating a shaded ceramic block as disclosed herein. An exemplary process involves taking an image of the defective tooth area. This image may be used to import the data into a computer and proprietary software may be used to create a virtual restoration. The software may then send this virtual data to a milling chamber where the dental restoration is carved out of a solid block of, for example, composite resin or porcelain. The resultant restoration can then be adjusted in the patient's mouth and bonded in place.

If porcelain is used, practitioners may treat the restoration with stains and glazes and subsequent heat treatments to both beautify and strengthen the definitive restoration prior to bonding. Practitioners may perform acid etching of both the underside of the restoration and the topside of the tooth itself, which may microscopically increases surface area on both opposing surfaces. Practitioners may then use composite resin materials to fuse the resultant restoration to the tooth, completing the restoration process.

Currently, using available methods, staining and glazing to match the patient's natural tooth color is a complicated and time consuming process. For example, in order to achieve a natural appearance of the restoration, the tooth color and the translucence must be simulated over several layers. For example, practitioners may use intermediate layers such as dye pastes or dye suspensions, which may require several applications, each application requiring and individual setting and drying time. After several procedures, the restoration may be fired in an oven. This process is time- and cost-intensive.

In another method, described in U.S. Pat. No. 6,709,694, color reagents are dissolved in water. Ceramic restorations are then steeped in the reagent for 5 minutes and then dried and sintered. Finally, after the steeping and drying times, the restoration may be dried and sintered.

In another method and system, provided by VITA, a restoration is dipped into the coloring liquid and dried. Each application requires a color reaction time and a color drying time. The method also includes steps of prebaking and preheating and requires the use of hydrochloric acid. Available coloration liquids, such as but not limited to the VITA liquids are thick and they do not penetrate the ceramic.

The formulation of the disclosed system of compositions provides a unique and surprising feature of requiring no drying time between the application of layers.

The disclosed technology may enable the dentist, dental technician, or ceramist to reproduce the subtleties of natural dentition, for example, matching a zirconia crown to a natural root. Furthermore, the technology may disguise opacity, and may enhance translucency, and may provide subtle characterization for a natural looking result.

The technology may be supplied in a kit, for example, a kit that contains one of about 5, 10, 15, 20, 25, 30, or more shades. The kit may also include a shade guide which is matched to the shades of the system. The kit may also include a thinner.

Ceramic Block Technology

CAD/CAM restorations may be milled from solid blocks of white composite resin such as ceramic, for example but not limited to Zirconia Ceramic. Currently, ceramic blocks, for example, Zirconia Ceramic blocks, are provided in opaquish white. Some have attempted to create solid blocks of ceramic material that are pre-colored with a dentin color. However, the known colored blanks are still opaque and unnatural in appearance. The present invention uses the quality of the disclosed coloring systems to impart a natural appearance to the ceramic block. For example but not limited to, the present coloring system uses novel compositions to impart a slight bluish tint contained in natural tooth enamel color. While color matching using the coloring systems disclosed herein may still be used, preparing ceramic blocks by the coloring method described herein may significantly reduce the underlying opaqueness of the block and may therefore require for creating the appearance of translucence, less post cutting and pre- and post-sintering coloring steps because there is less opaqueness to overcome.

We disclose herein a method of obtaining a natural, tooth-like enamel appearance with more translucency than currently available in the art, by baking dentin color glass ceramic into zirconia.

The known colored zirconia blanks simulate natural dentin rather than simulating the translucence of the outer layers, for example, the enamel of the tooth. Dentin is the second layer of a natural tooth, which may be softer, more porous, and darker than the hard, dense, semi-translucent outer layer of enamel which protects it. The development of a colored zirconia blank that simulates the translucent layer, for example, the enamel of the tooth is novel and only possible since the disclosed invention of the coloring systems which impart translucence to zirconia, which until the novel disclosure herein was impossible. Additionally, prior to the invention disclosed herein, several layers of outer ceramic were necessary to prepare a zirconia restoration, therefore only dentin color was sought after. Now that the inventor has discovered how to impart translucency to zirconia ceramic, less cutting is needed leading to less invasive dentistry.

In one variation of the method of creating an enamel colored zirconia block, before being pressed into blanks, zirconia powder is mixed with color pigment powder as disclosed herein. The color pigment disclosed herein may act as an opacifier. Translucency may be optimized by using the smallest particle sizes and minimum amounts of color pigments. By mixing the color pigments disclosed herein with the zirconia powder prior to pressing the zirconia into blanks, translucency may be achieved. Translucency may be increased, for example, by using the smallest possible particle sizes (e.g., nanosize particles) and minimum amounts of color pigments. This may be achieved, for example but not limited to, by performing serial dilutions of the pigment until the desired coloring is achieved.

In a second variation, an enamel colored zirconia blank is prepared by a doping method. In this method, the block is prepared by dissolving metallic coloring substances, for example but not limited to, manganese nitrate, cobalt nitrate, chromium nitrate, and/or iron nitrate into water, alcohol, or acid solution. The resolution solution may be referred to as reduced or doped and it may then be combined with a small amount of zirconia powder. The mixture of the zirconia powder and the metallic coloring substance may be allowed to dry. After drying, the resulting powder will be highly colored. The highly colored zirconia powder may then be blended into a large, production batch of zirconia powder and thereby diluted or serially diluted until the concentration for the desired level of color and translucency are reached. The resultant mixture may then be pressed into blanks resulting in enamel colored zirconia blanks.

In a third variation, an enamel colored zirconia blank may be prepared by a doping method. In all variations, the doping method may overcome the difficulties of obtaining consistent and/or homogenous color in a large batch of powder. By these methods, one may serially dilute the dyes and thereby create more consistent and/or homogenous color than might be achieved by merely adding a small amount of dye into a large zirconia lot. In this variation, metallic coloring substances such as but not limited to Nickel octanoate and/or copper carboxylate are dissolved in, for example but not limited to, mineral spirits, d-limonene, phytochemicals, phytooils, hydrocarbon solutions, 3-methoxy-3-methyl-1-butanol and similar dissolving agents. The dissolving agent may provide quicker and deeper penetration than traditional solutions such as alcohols. The result is a doped solution which may be mixed with a small amount of zirconia powder. The mixture may then be dried, or allowed to dry naturally. This may result in a highly colored batch of zirconia powder which may then be blended into a large, production batch of zirconia powder and then pressed into blanks.

In another variation, an already made zirconia block may be immersed in the liquid coloring agents disclosed herein until full absorption is achieved and then may be allowed to dry. For example, the zirconia block may be immersed in the solutions disclosed herein for, for example but not limited to, about one day to about 5 days, about one day to about four days, or about one day to about three days.

In a variation, a method of producing an enamel colored zirconia mill blank, includes the steps of creating a concentrated enamel shaded pigment as discussed herein or otherwise known in the art. Dissolving the concentrated enamel shaded pigment in one of hydrocarbons, mineral spirits and phyto-oils. Examples of hydrocarbons as diluting agents include d-limonene, plant derived oils, lavendar oil, 3-methyl-1-butanol, and mineral oil. The concentrated enamel shaded pigment is then combined with a small amount of unpigmented zirconia powder. The unpigmented zirconia powder may be diluted in a step wise fashion into larger amounts of unpigmented zirconia powder to result in a enamel color shaded powder for pressing. The enamel color shaded powder for pressing (and in turn, the resulting mill blank) may comprise a considerably reduced concentration of starting materials. As an example, the concentrated enamel shaded pigment (e.g., the enamel shaded pigment created prior to serial (e.g., step wise) dilution) may contain 1X of a component. The component here may be any component disclosed herein. 1X may represent the total amount of that component in the mixture, for example, 1X may represent 2.3 milligrams or 3.5 nanograms, depending on the actual amount of the component present. As the concentrated enamel shaded pigment is mixed in a step wise fashion into serial batches of unpigmented zirconia powder, the ultimate concentration of the component decreases by the dilution factor at east step. For example, one may begin with 10 grams of full concentrated enamel shaded pigment. One may remove one gram of the full concentrated enamel shaded pigment and add it to 9 grams of unpigmented zirconia. After thoroughly mixing the shaded pigment with the unpigmented zirconia, such that the shaded pigment is thoroughly and evenly dispersed, the result is a pigmented zirconia powder containing 0.1X of the component of the mixture (and in fact, of all components in the mixture). The process continues in a step wise fashion, 1 gram of the newly formed mixture (wherein the components are present at an amount of 0.1X their original) is added to 9 grams of unpigmented zirconia. The process continues until the ultimate concentration of the components is and of 0.1X, or 0.01X, or $1\times10^{-2}$ X, $1\times10^{-3}$ X, or $1\times10^{-4}$ X, or $1\times10^{-5}$ X, or $1\times10^{-6}$ X, or $1\times10^{-7}$ X, or $1\times10^{-8}$ X, $1\times10^{-9}$ X, $1\times10^{-10}$ X, $1\times10^{-11}$ X, $1\times10^{-12}$ X, $1\times10^{-13}$ X, $1\times10^{-14}$ X, $1\times10^{-15}$ X, $1\times10^{-16}$ X, $1\times10^{-17}$ X, $1\times10^{-18}$ X, $1\times10^{-19}$ X, $1\times10^{-20}$ X, $1\times10^{-21}$ X, $1\times10^{-22}$ X, $1\times10^{-23}$ X, $1\times10^{-24}$ X, v $1\times10^{-25}$ X, $1\times10^{-26}$ X, $1\times10^{-27}$ X, $1\times10^{-28}$ X, v $1\times10^{-29}$ X, $1\times10^{-30}$ X, $1\times10^{-31}$ X, $1\times10^{-32}$ X, $1\times10^{-33}$ X, $1\times10^{-34}$ X, $1\times10^{-35}$ X, $1\times10^{-36}$ X, or $1\times10^{-37}$ X.

The resulting zirconia powder ready for pressing into a block may therefore me about 60.00 to 99.99999999 wt % dental zirconia powder. In another example, the resulting zirconia powder ready for pressing may be 70.00 to 99.99999999 wt % dental zirconia powder, 80.00 to 99.99999999 wt % dental zirconia powder, 81.00 to 99.99999999 wt % dental zirconia powder, 82.00 to 99.99999999 wt % dental zirconia powder, 83.00 to 99.99999999 wt % dental zirconia powder, 84.00 to 99.99999999 wt % dental zirconia powder, 85.00 to 99.99999999 wt % dental zirconia powder, 86.00 to 99.99999999 wt % dental zirconia powder, 87.00 to 99.99999999 wt % dental zirconia powder, 88.00 to 99.99999999 wt % dental zirconia powder, 89.00 to 99.99999999 wt % dental zirconia powder, 90.00 to 99.99999999 wt % dental zirconia powder, 91.00 to 99.99999999 wt % dental zirconia powder, 92.00 to 99.99999999 wt % dental zirconia powder, 93.00 to 99.99999999 wt % dental zirconia powder, 94.00 to 99.99999999 wt % dental zirconia powder, 95.00 to 99.99999999 wt % dental zirconia powder, 96.00 to 99.99999999 wt % dental zirconia powder, 97.00 to 99.99999999 wt % dental zirconia powder, 98.00 to 99.99999999 wt % dental zirconia powder, 99.00 to 99.99999999 wt % dental zirconia powder, and intervals between each of these.

In another variation, a method of producing an enamel colored zirconia mill blank, may include the following steps. An enamel shaded pigment may be created with at least one metal nitrated. The metal nitrate may include one or more of manganese nitrate, cobalt nitrate, chromium nitrate, and iron nitrate. The enamel shaded pigment is dissolved a dissolving such as water, alcohol and acid. The enamel shaded pigment is combined with an amount of unpigmented zirconia powder to create a concentrated enamel shaded zirconia. The mixture is dried resulting in a concentrated enamel colored zirconia powder. The resulting enamel colored zirconia powder is then step wise diluted as above. After thoroughly mixing the shaded pigment with the unpigmented zirconia, such that the shaded pigment is thoroughly and evenly dispersed, the result is a pigmented zirconia powder containing 0.1X of the component of the mixture (and in fact, of all components in the mixture). The process continues in a step wise fashion, 1 gram of the newly formed mixture (wherein the components are present at an amount of 0.1X their original) is added to 9 grams of unpigmented zirconia. The process continues until the ultimate concentration of the components is and of 0.1X, or 0.01X, or $1\times10^{-2}$ X, $1\times10^{-3}$ X, or $1\times10^{-4}$ X, or $1\times10^{-5}$ X, or $1\times10^{-6}$ X, or $1\times10^{-7}$ X, or $1\times10^{-8}$ X, $1\times10^{-9}$ X, $1\times10^{-10}$ X, $1\times10^{-11}$ X, $1\times10^{-12}$ X, $1\times10^{-13}$ X, $1\times10^{-14}$ X, $1\times10^{-15}$ X, $1\times10^{-16}$ X, $1\times10^{-17}$ X, $1\times10^{-18}$ X, $1\times10^{-19}$ X, $1\times10^{-20}$ X, $1\times10^{-21}$ X, $1\times10^{-22}$ X, $1\times10^{-23}$ X, $1\times10^{-24}$ X, v $1\times10^{-25}$ X, $1\times10^{-26}$ X, $1\times10^{-27}$ X, $1\times10^{-28}$ X, v $1\times10^{-29}$ X, $1\times10^{-30}$ X, $1\times10^{-31}$ X, $1\times10^{-32}$ X, $1\times10^{-33}$ X, $1\times10^{-34}$ X, $1\times10^{-35}$ X, $1\times10^{-36}$ X, or $1\times10^{-37}$ X.

In another variation, a method of producing an enamel colored zirconia mill blank, may include the following steps. An enamel shaded pigment may include, among other components, at least one of nickel octanoate and copper carboxylate. The enamel shaded pigment may be dissolved in one or more of hydrocarbons, mineral spirits and/or phyto-oils. The resulting enamel shaded pigment mixture may be combined with a small amount of unpigmented zirconia powder to create a concentrated enamel shaded zirconia. The mixture is dried resulting in a concentrated enamel colored zirconia powder. The resulting enamel colored zirconia powder is then step wise diluted as above. After thoroughly mixing the shaded pigment with the unpigmented zirconia, such that the shaded pigment is thoroughly and evenly dispersed, the result is a pigmented zirconia powder containing 0.1X of the component of the mixture (and in fact, of all components in the mixture). The process continues in a step wise fashion, 1 gram of the newly formed mixture (wherein the components are present at an amount of 0.1X their original) is added to 9 grams of unpigmented zirconia. The process continues until the ultimate concentration of the components is and of 0.1X, or 0.01X, or $1\times10^{-2}$ X, $1\times10^{-3}$ X, or $1\times10^{-4}$ X, or $1\times10^{-5}$ X, or $1\times10^{-6}$ X, or $1\times10^{-7}$ X, or $1\times10^{-8}$ X, $1\times10^{-9}$ X, $1\times10^{-10}$ X, $1\times10^{-11}$ X, $1\times10^{-12}$ X, $1\times10^{-13}$ X, $1\times10^{-14}$ X, $1\times10^{-15}$ X, $1\times10^{-16}$ X, $1\times10^{-17}$ X, $1\times10^{-18}$ X, $1\times10^{-19}$ X, $1\times10^{-20}$ X, $1\times10^{-21}$ X, $1\times10^{-22}$ X, $1\times10^{-23}$ X, $1\times10^{-24}$ X, v $1\times10^{-25}$ X, $1\times10^{-26}$ X, $1\times10^{-27}$ X, $1\times10^{-28}$ X, v $1\times10^{-29}$ X, $1\times10^{-30}$ X, $1\times10^{-31}$ X, $1\times10^{-32}$ X, $1\times10^{-33}$ X, $1\times10^{-34}$ X, $1\times10^{-35}$ X, $1\times10^{-36}$ X, or $1\times10^{-37}$ X.

In another variation, a method of producing an enamel colored zirconia mill blank, may include the following steps. An enamel shaded pigment may be created with at least one metal nitrated. The metal nitrate may include one or more of manganese nitrate, cobalt nitrate, chromium nitrate, and iron nitrate. The enamel shaded pigment is dissolved a dissolving such as hydrocarbons, phytooils, phytochemicals, mineral oil. The enamel shaded pigment is combined with an amount of unpigmented zirconia powder to create a concentrated enamel shaded zirconia. The mixture is dried resulting in a concentrated enamel colored zirconia powder. The resulting enamel colored zirconia powder is then step wise diluted as above. After thoroughly mixing the shaded pigment with the unpigmented zirconia, such that the shaded pigment is thoroughly and evenly dispersed, the result is a pigmented zirconia powder containing 0.1X of the component of the mixture (and in fact, of all components in the mixture). The process continues in a step wise fashion, 1 gram of the newly formed mixture (wherein the components are present at an amount of 0.1X their original) is added to 9 grams of unpigmented zirconia. The process continues until the ultimate concentration of the components is and of 0.1X, or 0.01X, or $1\times10^{-2}$ X, $1\times10^{-3}$ X, or $1\times10^{-4}$ X, or $1\times10^{-5}$ X, or $1\times10^{-6}$ X, or $1\times10^{-7}$ X, or $1\times10^{-8}$ X, $1\times10^{-9}$ X, $1\times10^{-10}$ X, $1\times10^{-11}$ X, $1\times10^{-12}$ X, $1\times10^{-13}$ X, $1\times10^{-14}$ X, $1\times10^{-15}$ X, $1\times10^{-16}$ X, $1\times10^{-17}$ X, $1\times10^{-18}$ X, $1\times10^{-19}$ X, $1\times10^{-20}$ X, $1\times10^{-21}$ X, $1\times10^{-22}$ X, $1\times10^{-23}$ X, $1\times10^{-24}$ X, v $1\times10^{-25}$ X, $1\times10^{-26}$ X, $1\times10^{-27}$ X, $1\times10^{-28}$ X, v $1\times10^{-29}$ X, $1\times10^{-30}$ X, $1\times10^{-31}$ X, $1\times10^{-32}$ X, $1\times10^{-33}$ X, $1\times10^{-34}$ X, $1\times10^{-35}$ X, $1\times10^{-36}$ X, or $1\times10^{-37}$ X.

In each of these, the hydrocarbon may be plant derived of man made. For example, the diluting agent may be d-limonene, lavendar oil, 3-methyl-1-butanol, or a combination of these.

Method of Using the System

The method of using the system may be as follows. However, other methods are foreseen, therefore the following is a non-limiting description of one method of using the system. The following steps do not require a specific order of execution by way they are presented, unless specified. The disclosed steps are listed as exemplary such that additional or different steps may be executed or the steps may be executed in a different order.

1. Prepare the Zirconia Surface

Dust may be removed from the zirconia understructure. For example, dust may be completely removed from the zirconia understructure, especially the inside incisal and angle regions. A firm bristled brush, for example but not limited to a CLEANUP BRUSH may be used to remove the dust.

Mark the regions to be stained, for example, the cervical, body, and incisal. Marking may be made on the surface of the zirconia, for example, using a graphite pencil. The marks may disappear during firing.

2. Select Your Colors

Choose coloring liquids suitable for the areas to be shaded. In one example, both the outer and inner surfaces of a zirconia understructure may be treated which may produce a translucent effect. In another example, when restoring discolored teeth, inner surfaces may not be stained which may help retain the original opacity of the zirconia.

Colors may be chosen by using a color guide which may be included, for example, with a kit of the system. In one example, the liquid compositions may be formulated to match the shades of, for example but not limited to, the VITA CLASSIC SHADE GUIDE.

For cervical, connector, and lingual regions of the zirconia understructure, one may choose a color one or two ranks darker than the reference shade. For example, if the reference color is A2, one may choose the shade of the system referenced by A3 or A3.5. For incisal regions, one may choose Incisal Light or Incisal Dark of the system.

3. Apply Colors

Each color liquid of the system may be shaken well before using. One may apply the color using an applicator brush. The applicator brush may be dipped into the liquid of the system and any excess color may be removed against the edge of the bottle.

The color liquid of the system may be applied quickly to unsintered zirconia. Unsintered zirconia is porous and may absorb more colorant than required if the applicator brush is held against its surface for too long. One may elect to treat the incisal portion of the understructure before the body portion. This may prevent surfacing of the darker body color.

The dipping and painting with the disclosed liquid may be effective after a 1 second application and subsequent layers may be applied with no drying time in between. The disclosed colorant may penetrate through a 3 mm or larger sample with no preheating required. The disclosed colorant may be used at room temperature or may be used at 300° C. or any other temperature. After application of the disclosed colorant, the restoration, such as a Zirconia restoration, may be sintered in an oven that naturally increases from approximately 300° C. to approximately 1380° C. over a period of about 7-about 8 hours. Depending on the nature of the equipment used, longer or shorter periods may be applied.

One may use a brush, including but not limited to, the STAIN BRUSH or the TOUCHUP BRUSH and may apply for example, at least one coat, at least two coats, or at least three coats (or more) of the chosen liquid composition, for example, Incisal Light or Incisal Dark liquid, to the margins and occlusal surfaces. Applying the liquid in vertical strokes may prevent the appearance of horizontal stripes.

The reference body color may be applied to the remaining surfaces at least one, two or three times. Additional applications may be desired, for example, if the zirconia understructure is relatively thick.

4. Sinter

The system may not require prefiring. The normal sintering process may proceed as soon as the zirconia surface is dry to the touch.

Process

Each ingredient may be measured very accurately by weight and not by volume. For the solutions that are made with a very low percentage of raw materials compared to diluent. The raw materials may be diluted with a hydrocarbon, mineral oil, phyto-oil (e.g., an oil derived from a portion of a plant), phyto-chemical, or phytol, (or agent with similar chemical properties) such as but not limited to lavendar oil, spike lavendar oil or D-Limonene, for example but not limited to, dilutions of 5, 10, 20, 30, 40, 50, 60, 70, 80, 90 or 100 times or more or less than measured before mixing with other ingredients. This stage should be performed without the application of heat. Phyto-oils, phyto-chemicals, hyrdrocarbons, and phytols, such as D-Limonene, lavendar oil, and 3-methyl-1 butanol are novel and unique diluents that are not used by others in the dental arts. Replacement of more typical diluents such as alcohols and acids, may produce a product that is more biocompatible. It may also produce a product that is less toxic and therefore more amenable to shipping by air and internationally. D-Limonene may be replaced by other phyto-oils (or agent with similar chemical properties).

Quality Control

After each color solution has been mixed, one may take a thin, pre-sintered, sample of zirconia, for example an approximately 0.5 mm×10 mm×20 mm in size sample, and may dip/soak it in the solution for up to about 10 seconds.

After applying the sample color, quickly remove and excess color solution from the zirconia sample, for example, using an air gun or a piece of tissue paper.

Take the liquid color treated zirconia sample to the sintering over and heat it at normal temperature for zirconia sintering program process. The heat should be for example but not limited to 1500+/−Celsius. After sintering, allow the treated zirconia chip to cool to room temperature. Examine the color of the sintered zirconia.

Each batch of colorant solution may be checked to insure color quality and uniformity. Slight variations of color may occur between different batches that are mixed, and/or if the raw materials are acquired from different suppliers or vendors.

Technical Specifications

For the solutions that are made with a very low percentage of raw materials, the raw material may be diluted with e.g., phyto-oils, phyto-chemicals, phytols, hydrocarbons, or D-Limonene for example but not limited to, dilutions of 5, 10, 20, 30, 40, 50, 60, 70, 80, 90 or 100 times or more or less, and then measured before mixing with other ingredients.

The Coloration process formulary may include the following: Chromium 2-Ethylhexanoate, Iron 2-Ethylhexanoate, Cobalt 2-Ethylhexanoate, Manganese 2-Ethylhexanoate, Copper 2-Ethylhexanoate, Zirconia Carboxylate, Yttrium Carboxylate, Zinc 2-Ethylhexanoate, phyto-oil such as D-Limonene: formula: C10H16 (natural) CAS#5989-27-5 TSCA; Soya Ester (Natural), Mineral Spirit (Petroleum HydroCarbon).

For example, Coloring Material Ingredients may include: 6% Iron Hex-Cem Solution, 8% Chromium Hex-Cem, 24% Zirconia Hex-Cem, 6% Manganese Hex-Cem, 8% Nickel Hex-Cem, and/or 6% Cobalt Hex-Cem. Ingredients may also include D-Limonene Hydrocarbon.

As another example, a base formula may include, among other things, D-Limonene, Mineral spirits, and zirconia hex cem 24% and one or more of the following: chromium hex cem 8%, cobalt hex cem 6%, iron hex cem 6%, nickel II octanoate, and manganese II ethylhexanoate.

The following formulary chart provides an exemplary system of coloration liquids. These are for illustrative purposes only and are not limiting.

TABLE ONE

|  | A1 | A2 | A3 | A3.5 | A4 |
|---|---|---|---|---|---|
| Fe | 4.0-6.0% | 8.5-10.5% | 11-15% | 16-20% | 20%-23% |
| Cr | 0.01-1.0% | 0.01-1.0% | 0.01-1.20% | 0.01-1.5% | 0.01-1.3 |
| Zr | 3.0-5.0% | 4.5-7.0% | 4.5-6.5% | 3.0-7.0% | 4.0-6.5% |
| Mn | 0.0-1.5% | 0.0-1.5% | 0.0-1.5% | 0.0-1.5% | 0.001-1.0% |
| Ni | 0.0-1.5% | 0.0-1.5% | 0.0-1.5% | 0.0-1.5% | 0.0-1.5% |
| D-Limonene | balance | balance | balance | balance | balance |

TABLE ONE-continued

|   | B1 | B2 | B3 | B4 | Occlusal |
|---|---|---|---|---|---|
| Fe | 4.0-7.0% | 6.5-10.5% | 10-15% | 16-22% | 35-45% |
| Cr | 0.0-1.5% | 0.0-1.5% | 0-0.5% | 0.0-1.5% | 0.01-1.3 |
| Zr | 3.0-5.0% | 4.5-7.0% | 4.5-6.5% | 0.0-1.5% | 4.0-7.5% |
| Mn | 0.0001-1.0% | 0.001-1.0% | 0.0001-0.5% | 0.0-1.0% | 0.0-1.0% |
| Ni | 0.01-1.0% | 0.01-1.2% | 0.10-2.0% | 0.0-1.5% | 0.0-1.5% |
| D-Limonene | balance | balance | balance | balance | balance |

|   | C1 | C2 | C3 | C4 | D2 |
|---|---|---|---|---|---|
| Fe | 7.5-10.5% | 14.5-18% | 15-19% | 16-22% | 4.0-6.5% |
| Cr | 0.0-1.5% | 0.0-1.5% | 0-0.5% | 0.0-1.5% | 0.0001-1.0% |
| Zr | 3.0-6.0% | 4.0-7.0% | 4.0-6.5% | 4.0-7.0% | 3.0-6.0% |
| Mn | 0.0001-1.0% | 0.0-1.0% | 0.0-1.0% | 0.01-1.2% | 0.0-1.2% |
| Ni | 0.00-1.0% | 0.0-1.2% | 0.0-1.2% | 0.0-1.2% | 0.0-1.2% |
| Co | 0.00-1.0% | 0.0-1.2% | 0.0-1.2% | 0.0-1.2% | 0.0-1.2% |
| D-Limonene | balance | balance | balance | balance | balance |

|   | D3 | D4 | Inc Light | Inc Dark | Pink |
|---|---|---|---|---|---|
| Fe | 7.5-10.5% | 8.5-12% | 0-1.2% | 0-1.2% | 0.0-1.2% |
| Cr | 0.01-1.5% | 0.0-1.5% | 0-1.2% | 0-1.2% | 0.0-1.2% |
| Zr | 3.0-6.0% | 4.0-7.0% | 1.0-4.5% | 2.0-6.0% | 0.0-1.2% |
| Mn | 0.0001-1.0% | 0.0-1.0% | 0-1.0% | 0.01-1.2% | 0.0-1.2% |
| Ni | 0.00-1.0% | 0.0-1.2% | 0.01-3.2% | 0.01-2.2% | 0.0-1.2% |
| Co | 0.00-1.0% | 0.0-1.2% | 0.0-1.2% | 0.0-1.2% | 1.0-4.5 |
| D-Limonene | balance | balance | balance | balance | balance |

Each ingredient must be measured by weight, not by volume.

The following formulary chart provides a second exemplary system of coloration liquids. These are for illustrative purposes only and are not limiting.

|   | A1 | A2 | A3 | A3.5 | A4 |
|---|---|---|---|---|---|
| Fe | 5.0-6.0% | 9.0-10.5% | 13-14.2% | 18-19% | 20.5-21.9% |
| Cr | 0.001-0.70% | 0.01-0.80% | 0.01-0.90% | 0.01-.90% | 0.10-1.3% |
| Zr | 3.5-4.5% | 4.5-6.7% | 5.3-6.2% | 5.0-6.25% | 5.0-6.2% |
| Mn | — | — | — | — | 0.001-0.6% |
| Ni | — | — | — | — | — |
| D-Limonene | balance | balance | balance | balance | balance |

|   | B1 | B2 | B3 | B4 | Occlusal |
|---|---|---|---|---|---|
| Fe | 5.0-6.0% | 8.0-9.2% | 11-12.4% | 18.5-20% | 35-45% |
| Cr | — | — | — | — | 0.01-1.3 |
| Zr | 3.5-4.5% | 5.3-6.3% | 5.1-6.1% | — | 5.5-6.5% |
| Mn | 0.0001-0.5% | 0.00001-0.010% | 0-0.10% | 0.0001-0.10% | — |
| Ni | 0.10-1.0% | 0.1-1.1% | 0.10-1.25% | 0.10-1.25% | — |
| D-Limonene | balance | balance | balance | balance | balance |

|   | C1 | C2 | C3 | C4 | D2 |
|---|---|---|---|---|---|
| Fe | 8.5-9.5% | 15.5-16.5% | 16.5-17.5% | 20.5-21.5% | 5.1-6.2% |
| Cr | — | — | — | — | 0.01-1.0% |
| Zr | 4.5-5.5% | 4.5-5.5% | 4.5-5.5% | 4.5-5.5% | 3.5-4.9% |
| Mn | 0.0001-0.6% | 0.01-0.75% | 0.10-0.8% | 0.01-1.9% | — |
| Ni | — | — | — | — | — |
| Co | — | — | — | — | — |
| D-Limonene | balance | balance | balance | balance | balance |

|   | D3 | D4 | Inc Dark | Inc Light | Pink |
|---|---|---|---|---|---|
| Fe | 9.0-10.0% | 10-11% | — | — | — |
| Cr | 0.10-1.0% | — | — | — | — |

-continued

| | | | | |
|---|---|---|---|---|
| Zr | 4.5-5.5% | 4.5-5.5% | 1.75-2.5% | 3.5-4.5% | — |
| Mn | 0.001-0.5% | 0.001-0.60% | 0-1.0% | 0.01-0.8% | — |
| Ni | — | 0.01-0.95% | 2.0-3.2% | 0.0-1.5% | — |
| Co | — | — | — | — | 2.0-3.0% |
| D-Limonene | balance | balance | balance | balance | balance |

Each ingredient must be measured by weight, not by volume.

The liquid composition may not use water or alcohol as a solvent. Rather, the liquid composition may use a phytooil, a phytochemical, a hydrocarbon, D-Limonene, lavendar oil, and similar as a solvent. The discovery of the disclosed ingredient ranges and formulations took many years and has not been discovered by others in the art. While some of the basic underlying ingredients have been used by others in the art, none have successfully arrived at a liquid composition that provides the level of realistic coloring of zirconia ceramics, much less provided the ability to produce fine matching, high efficiency production, and absorbancy, as the disclosed system and methods.

Figure 2:
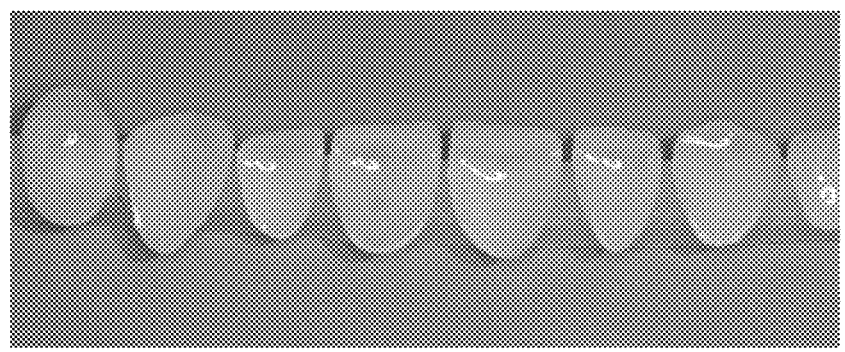
FIG. 2 illustrates the thickness of restorations.
Figure 2:
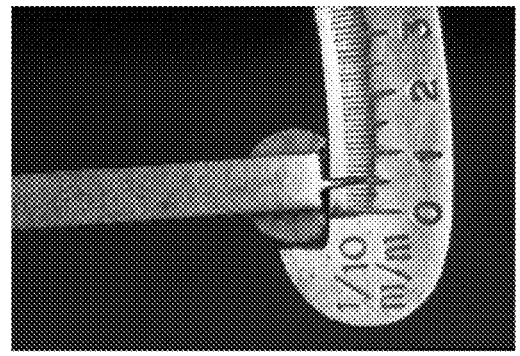
Figure 3:
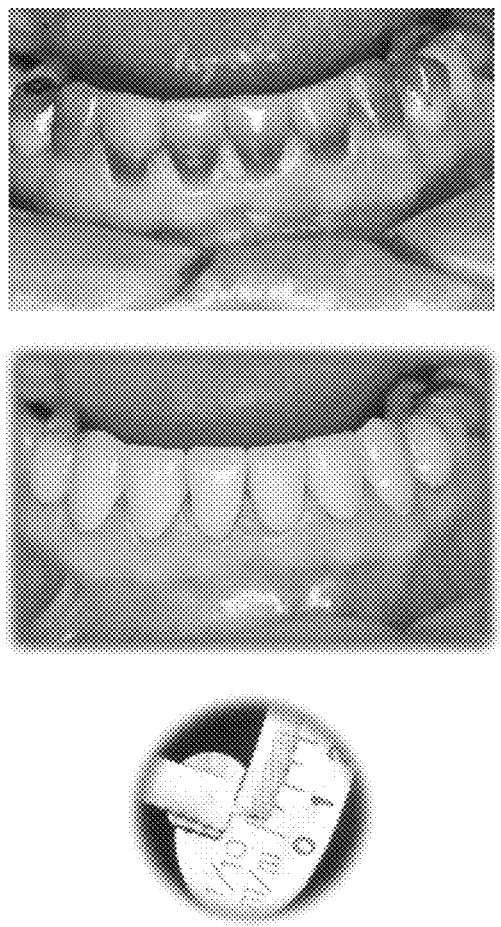
FIG. 3 illustrates the success of the thin restoration in masking underlying color defects.
Figure 4:
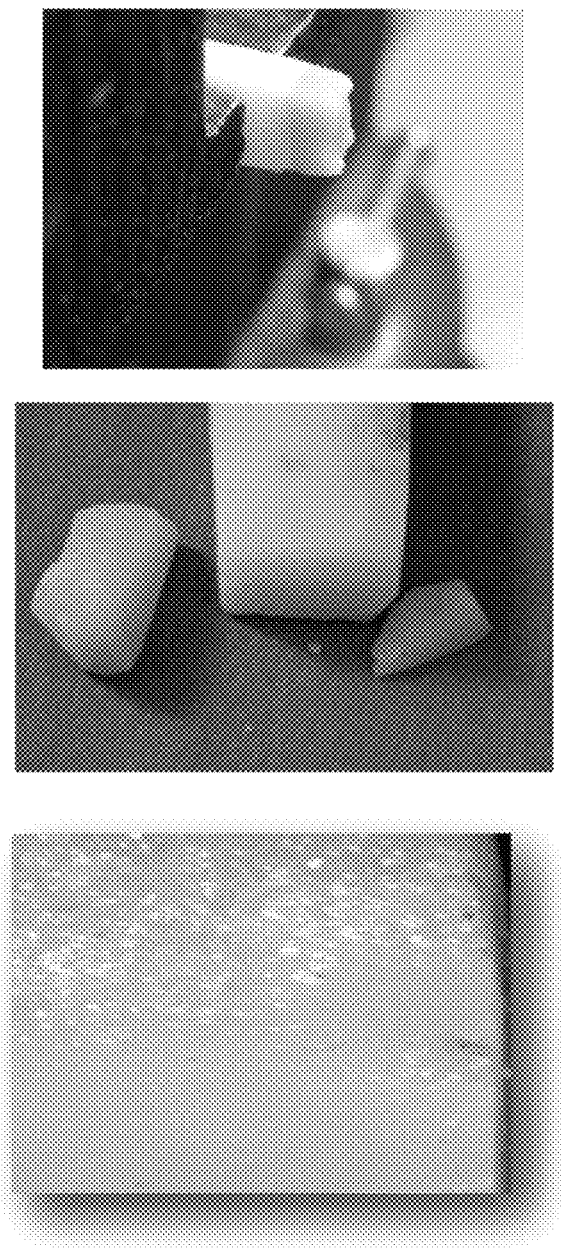
FIG. 4 illustrates the absorption of the disclosed composition.

Use of the disclosed coloring system may allow for prosthesis, crowns, and restorations that measure less than 0.5 mm in thickness as demonstrated in FIG. 2. They may further create translucence and natural color matching on a "contact lens" thickness of restoration material. FIG. 3 provides an example of the result of application of the disclosed color system. In the example of FIG. 3, the restoration showed natural color and translucence, and no shadow or show through of the underlying discoloration, even at a restoration thickness of 0.1 mm. FIG. 4 demonstrates the penetration of the colorant liquid of the disclosed system.

The disclosed solutions may be used at further dilutions. For example but not limited to, in one variation, the disclosed solutions may be used at a 6% solution or may be diluted another 10%, the solutions may be applied in highly diluted form.

Commonly, it is understood that no dyes will adhere to Zirconia/yttrium ceramics due to the strength of the material. All currently marketed dye solutions rely upon applications during the pre-sintered or absorbant stage of the material. The dyes that are currently available are $O_2$ sensitive and they are also degraded rapidly at temperatures over 900° C. Surprisingly, the disclosed compositions and systems which were developed after years of detailed study, bond to the Zirconia/yttrium restoration at temperatures over 900° C. without losing pigment. While the basic use of metal ions and metal complexes has been broadly disclosed for use in coloring ceramics, there has been no enabling disclosure of the effective concentrations, and it took Applicant many years of trial and error to determine the optimal ratios as well as the optimal solvents that would actually stain ceramics, such as zirconia ceramics. Flourescence may be added to make the tooth look more natural. For example, flourescense may be added with down to 0.01% glassy ceramic. Furthermore, while in the knowledge of the art, ceramic does not bond to Zirconia, it has been demonstrated that use of the disclosed liquid colorant compositions may permit bonding the glassy ceramic layer to Zirconia under certain circumstances.

Post Sintering Color Correction

A second system and compositions are disclosed which may be used to adjust and correct color after sintering of the restoration. Often, because of the great expense of technology such as the CAD/CAM machine, practitioners have restorations made off site. Often, although the practitioner performed careful color matching, the final restoration does not provide the appropriate natural appearance and does not blend in with the natural dentature.

It is thought in the art that post-sintering coloration of zirconia is impossible. Therefore, it was a unique and surprising result that with the disclosed system, even zirconia restorations may be color adjusted after sintering. The color powders of the post-sintering system allow for high temperature zirconia/porcelain color modification. The powders and available in a wide range of colors and allow formulation of most tooth and tissue shades straight from the bottle or in combination.

Another surprising result is that, with the post-sintering coloration system and compositions disclosed herein, there is no need to sandblast the post-sintered restoration. The disclosed coloration system bonds even to the smoothest of zirconia surfaces and laminating porcelain chemically bonds to the disclosed coloration system of stains.

The post-sintering coloration stains disclosed herein chemically bond to sintered zirconia after backing. The coloration system or stains may be supplied as a series of powders. The powders may be diluted using any standard dental solvent and then applied to the sintered zirconia restoration to fine tune the color and affect more natural color matching or correct any color deficiencies or inaccuracies. After the stains have been applied to the surface of the restoration, the restorations may be baked, under vacuum. The temperature may be increased by 40° C. per minute until reaching 1000° C.; may be airbaked at approximately 1000° C. for approximately 1 minute. The disclosed stains may also be used with conventional porcelains in the 850° C. to 950° C. range.

The coloring solutions may include, for example, Calcium Tungstate in a range of 0.1% to 4.0% of the pigment/glass ceramic mixture, a color ingredient as displayed below in a concentration that may vary depending on the desired shade, and a glass ceramic which may be, for example but not limited to Ferro 90-328-F, Ferro 10-115-D, and or a glass ceramic of the formula disclosed in Table Three. As an example, light pink (See Table TWO) may be mixed with 25 grams of Mason 6001 and 75 grams of Ferro-90-328F—for a total of 100 grams. To that mixture, 0.1% to 4% of Calcium Tungstate may be introduced. If a 3% Calcium Tungstate was introduced, the resultant coloring agent would comprise 25 grams Mason 6001, 75 grams of Ferro 90-328F and three grams of Calcium Tungstate which translates to 24.3% Mason 6001, 72.8% Ferro 90-328F, 2.9% calcium tungstate.

The chart below provides exemplary concentrations and sources for the various colors provided in an exemplary post-sintering coloration kit. Each of the below formulas below represent the color ingredient for each respective color.

TABLE TWO

| # | COLOR | INGREDIENT | % | ZirChrome Suppliers List |
|---|---|---|---|---|
| 00 | CLEAR | e.g., FERRO 10 115-D, Ferro 90-328F | | Ferro Corp Dinnerware Systems 4150 East 56th Street Cleveland OH 44105 Phone: 216-641-8580 Fax: 216-750-7519 |
| 01 | WHITE | MASON 6700 | 30.00% | |
| 11 | LIGHT BLUE | PEACOCK B-214 | 6.25% | |
| 12 | PINK BLUE | PEACOCK B-214 | 6.25% | Mason Color Works Inc 250 East Second Street P.O. Box 76 East Liverpool, OH 43920-5076 Phone: 330-385-4400 Fax: 330-385-4488 |
| | | FERRO C-1802-EZ | 2.00% | |
| 13 | GREY BLUE | PEACOCK B-214 | 6.25% | |
| | | PEACOCK Y-3822-A | 2.50% | Peacock Colors Inc 1000 National Avenue Addison, IL 60101-3175 Phone: 630-628-1960 Fax: 630-628-0420 |
| 21 | LIGHT PINK | MASON 6001 | 25.00% | |
| 22 | DARK PINK | FERRO C-1802-EZ | 12.00% | |
| 41 | YELLOW | PEACOCK Y-3849 | 15.00% | |
| 51 | BODY ORANGE | MASON 6001 | 16.00% | |
| | | PEACOCK Y-3849 | 5.00% | |
| 52 | DEEP ORANGE | FERRO C-1802-EZ | 6.00% | |
| | | PEACOCK Y-3849 | 10.00% | |
| 53 | OCHRE | PEACOCK Y-3822-A | 8.00% | |
| | | PEACOCK B-214 | 0.30% | |
| 54 | OLIVE | PEACOCK Y-3822-A | 12.00% | |
| | | PEACOCK B-214 | 2.50% | |
| 71 | LIGHT BROWN | PEACOCK T-4679 | 12.50% | |
| 72 | DARK BROWN | PEACOCK T-4679 | 12.50% | |
| | | PEACOCK B-214 | 3.00% | |
| 73 | CHARCOAL BROWN | PEACOCK T-4679 | 12.00% | |
| | | PEACOCK B-214 | 8.00% | |
| 91 | GREY | PEACOCK B-214 | 9.00% | |
| | | PEACOCK Y-3822-A | 6.00% | |
| | | FERRO C-1802-EZ | 5.00% | |

The balance of the ingredient mixture for the above powders may be a glass ceramic, dilutant and/or flow agent. For example, the glass ceramic, dilutant and/or flow agent may have the following composition:

TABLE THREE

| | |
|---|---|
| Si | 53.073% |
| Ca | 23.230% |
| K | 12.840% |
| Al | 9.450% |
| Ba | 0.492% |
| Pb | 0.317% |
| Fe | 0.162% |
| Zn | 0.129% |
| Zr | 0.117% |
| Ti | 0.101% |
| Rb | 0.039% |
| Sr | 0.035% |
| Cu | 0.015% |

Method of Restoration with Color

Currently dental restorations require 1 mm or greater reduction in the tooth enamel. Dental reductions of this gravity may result in secondary tooth decay due to the loss of integrity of the tooth as the reduction cuts very close to the pulp, allowing infection to enter the pulp area.

Historically, 22% of restored teeth decay after 5 years. The disclosed coloring system and method allows for good color control allowing for reduced reduction of tooth enamel during the preparation for applying restoration material. Under the disclosed method, tooth reduction may be less than 1 mm, less than 0.5 mm, or even less than 0.01 mm, while maintaining good coloration and natural appearance of the restoration.

Figure 5:
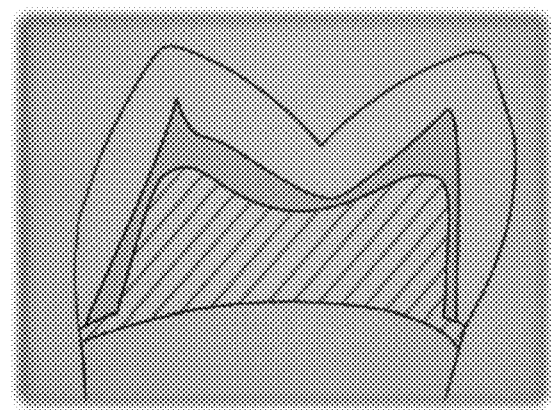
FIG. 5 illustrates the comparative protective properties of the disclosed system over the currently employed systems.
Figure 5:
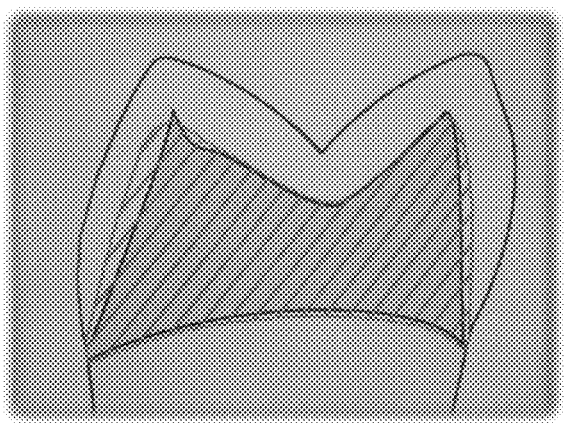

The Restoration system may be used, for example, for restoration crowns, bridges, or laminates. The method disclosed herein may include the following steps:

preparation of the tooth by reduction of about 0.001 mm-1.000 mm tooth enamel without approaching or compromising the pulp.

preparing the restoration by using the CAD/CAM or similar technologies using the presintering liquid disclosed herein to match the restoration to the natural color of the patient's existing teeth or to a color chosen by the patient or practitioner in the case of a full replacement sintering the restoration correcting the color using the post-sintering system disclosed herein covering the restoration with a glassy ceramic fitting the restoration to the patient's dentature FIG. 5 illustrates the improvement of the disclosed method and system over the currently used system. As seen, in the top drawing, traditional systems require numerous layers of material to create natural color. Therefore, the practitioner must remove enough tooth material to accommodate the multiple layers. This leaves a space between the pulp and the restoration, which may permit entry of infectious agents—leading to tooth decay. In the bottom drawing, we illustrate that under the disclosed system and method, the color system is robust enough that a very thin restoration may be used. This alleviates the need for multiple layers. In the improved method disclosed herein, the amount of tooth material a practitioner removes to accommodate the restoration is much smaller, for example about 0.001 mm-1.000 mm. As seen in FIG. 5B, there is no space between the restoration and the tooth and the pulp remains protected by the natural enamel. This small reduction and the maintenance of the natural enamel protects the pulp from infectious agents that cause decay.

Fluorescent Finish

Zirconia has no natural fluorescence. Therefore, although zirconia is a sought after material for dental restorations, it may be difficult to make the restoration look natural under all lighting conditions. For example, natural teeth have a natural fluorescence, which becomes apparent under, for example, black light. Zirconia restorations do not have any fluorescence under black light and instead appear shadowed, giving the appearance of missing teeth. The lack of flouresence may also contribute to zirconia's unnatural appearance under other types of household, indoor, outdoor (natural), industrial, and other types of synthetic and natural lighting.

We disclose a further material and system to impart a natural appearing fluorescence to ceramic restorations, for example, but not limited to, zirconia restorations. The following description discusses a method of applying fluorescence by brushing, dipping, or spraying a material onto the dental restoration. However, the same affect may be achieved by pressing the materials into the zirconia powder during zirconia block formation and production, i.e., into the raw materials that are used to create dental restorations.

In one variation, a material for producing a fluorescent appearance on a fluorescing, low-fluorescing, or non-fluorescing material, for example but not limited to a zirconia dental restoration, may have the following formula: Si: ~40%–~60%, Ca: ~10%–~30%, K: ~2%–~22%, Al: ~1%–~19%, CaW: ~1%–~14%, Ba: ~0%–~10%, Fe: ~0%–~10%, Zn: ~0%–~10%, Zr: ~0%–~10%, Ti: ~0%–~10%, Rb: ~0%–~10%, Sr: ~0%–~10%, Cu: ~0%–~10%.

In a second variation, a material for producing a fluorescent appearance on a fluorescing, low-fluorescing, or non-fluorescing material, for example but not limited to a zirconia dental restoration, may have the following formula: Si: ~45%–~55%, Ca: ~15%–~25%, K: ~7%–~17%, Al: ~5%–~14%, CaW: ~1%–~10%, Ba: ~0%–~5%, Fe: ~0%–~5%, Zn: ~0%–~5%, Zr: ~0%–~5%, Ti: ~0%–~5%, Rb: ~0%–~5%, Sr: ~0%–~5%, Cu: ~0%–~5%.

In a third variation, a material for producing a fluorescent appearance on a fluorescing, low-fluorescing, or non-fluorescing material, for example but not limited to a zirconia dental restoration, may have the following formula: Si: ~49–~51%, Ca: ~21%–~23%, K: ~11%–~13.5%, Al: ~8%–~9.5%, CaW: ~3.5%–~5%, Ba: ~0.01%–~1%, Fe: ~0%–~0.5%, Zn: ~0%–~0.5%, Zr: ~0%–~0.5%, Ti: ~0%–~0.5%, Rb: ~0%–~0.5%, Sr: ~0%–~0.5%, Cu: ~0%–~0.5%.

In a fourth variation, a material for producing a fluorescent appearance on a fluorescing, low-fluorescing, or non-fluorescing material, for example but not limited to a zirconia dental restoration, may have the following formula: Si ~50.073%, Ca ~22.230%, K ~12.840%, Al ~9.450%, CaW ~4.317%, Ba ~0.492%, Fe ~0.162%, Zn ~0.129%, Zr ~0.117%, Ti ~0.101%, Rb ~0.039%, Sr ~0.035%, Cu. ~0.015%

The material disclosed above may be used as a zirconia surface finish to impart, for example but not limited to, luster and a natural fluorescent appearance. The material disclosed above may have the further properties of being fired on the surface of a ceramic, for example but not limited to, a zirconia ceramic understructure as a bonding enhancer.

As discussed above, the disclosed material may be mixed into the ceramic powder during block formation, or may be applied after block cutting, after preliminary coloring, after secondary coloring, or at any other time during the preparation of the dental restoration. The material may be applied as an aerosol spray, may be brushed on as a liquid, or may be applied as a dipping agent. The material may be applied to both polished and unpolished surfaces with good result.

In one variation, the disclosed material may be applied by aerosol application as follows: (1) shake the aerosol can well until the mixing ball moves freely inside, (2) clean and prepare the ceramic surface, for example but not limited to, zirconia ceramic surface, (3) spray the material (which may be referred to alternatively as a glaze) approximately about 15 to about 20 cm from the restoration over dried, unfired stains, (4) remove stray, dry powder form undesired areas and margins with a brush, for example, but not limited to, the CLEANUP BRUSH, (5) fire.

The fluorescent finish may be prepared in either a high temperature or a low temperature version, with a fusing range of 750 degrees C. to 850 degrees C. for low temperature and a fusing range of 920 degrees C. to 990 degrees C. for a high temperature version.

In one variation the firing schedule may include the following steps: (1) pre-dry: 2 minutes, start temperature: 500° C., heating: 40° C. per minute, vacuum: 75 cmHg, start 500° C., Release: 920° C., Final Temp.: 990° C., Hold Time: 1 minute.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

I claim:

1. A method of producing an enamel colored zirconia mill blank, the method comprising:
    combining cobalt 2-ethyl hexanoate, iron 2-ethyl hexanoate, chromium 2-ethyl hexanoate, and nickel 2-ethyl hexanoate to create an enamel shaded pigment and dissolving the enamel shaded pigment in at least one component selected from the group consisting of hydrocarbons, mineral spirits and phyto-oils to produce a mixed enamel shaded pigment;
    combining the mixed enamel shaded pigment with an amount of unpigmented zirconia powder to create a concentrated enamel shaded zirconia;
    drying the concentrated enamel shaded zirconia to create a concentrated enamel colored zirconia powder;
    serially diluting the concentrated enamel colored zirconia powder into unpigmented zirconia powder to achieve a predetermined enamel color shaded powder;
    pressing the predetermined enamel color shaded powder to form a mill blank.

2. The method of claim 1 where the phyto-oil is selected from the group consisting of lavendar oil and d-limonene.

3. The method of claim 1 where the hydrocarbon is 3-methyl-1-butanol.

4. The method of claim 1 where the enamel shaded pigment is dissolved in a mixture comprising d-limonene and 3-mehtyl-1-butanol.

5. The method of claim 1 further wherein the enamel shaded pigment further comprises about 0.1% to about 0.4% calcium tungstate.

6. A method of producing an enamel colored zirconia mill blank, the method comprising:
    combining cobalt 2-ethyl hexanoate, iron 2-ethyl hexanoate, chromium 2-ethyl hexanoate, and nickel 2-ethyl hexanoate to create an enamel shaded pigment;
    the enamel shaded pigment with at least one component selected from the group consisting of manganese nitrate, cobalt nitrate, chromium nitrate, and iron nitrate;
    dissolving the enamel shaded pigment with at least one dissolving agent from the group consisting of water, alcohol and acid to produce a mixed enamel shaded pigment;
    combining the mixed enamel shaded pigment with an amount of unpigmented zirconia powder to create a concentrated enamel shaded zirconia;
    drying the concentrated enamel shaded zirconia to create a concentrated enamel colored zirconia powder;
    serially diluting the concentrated enamel colored zirconia powder into unpigmented zirconia powder to achieve a predetermined enamel color shaded powder;
    pressing the predetermined enamel color shaded powder to form a mill blank.

7. The method of claim 6 further wherein the enamel shaded pigment further comprises about 0.1% to about 0.4% calcium tungstate.

8. A method of producing an enamel colored zirconia mill blank, the method comprising:
   combining cobalt 2-ethyl hexanoate, iron 2-ethyl hexanoate, chromium 2-ethyl hexanoate, and nickel 2-ethyl hexanoate to create an enamel shaded pigment;
   creating an enamel shaded pigment consisting of at least one of Nickel octanoate and copper carboxylate;
   dissolving the enamel shaded pigment in at least one component selected from the group consisting of hydrocarbons, mineral spirits and phyto-oils to produce a mixed enamel shaded pigment;
   combining the mixed enamel shaded pigment with an amount of unpigmented zirconia powder to create a concentrated enamel shaded zirconia;
   drying the concentrated enamel shaded zirconia to create a concentrated enamel colored zirconia powder;
   serially diluting the concentrated enamel colored zirconia powder into unpigmented zirconia powder to achieve a predetermined enamel color shaded powder;
   pressing the predetermined enamel color shaded powder to form a mill blank.

9. The method of claim 8 where the phyto-oil is selected from the group consisting of lavendar oil and d-limonene.

10. The method of claim 8 where the hydrocarbon is 3-methyl-1-butanol.

11. The method of claim 8 where the enamel shaded pigment is dissolved in a mixture comprising d-limonene and 3-methyl-1-butanol.

12. The method of claim 8 further wherein the enamel shaded pigment further comprises about 0.1% to about 0.4% calcium tungstate.

\* \* \* \* \*